United States Patent [19]
Gordon

[11] 4,241,286
[45] Dec. 23, 1980

[54] WELDING HELMET LENS ASSEMBLY

[76] Inventor: Mack Gordon, 2905 Solon Rd., Cleveland, Ohio 44139

[21] Appl. No.: 867

[22] Filed: Jan. 4, 1979

[51] Int. Cl.³ .......................... B23K 9/32; A61F 9/06; G02F 1/13
[52] U.S. Cl. .......................................... 219/147; 2/8; 350/331 R
[58] Field of Search ........................ 219/147; 340/148; 350/331 R; 2/8, 427, 430, 431, 432

[56] References Cited

U.S. PATENT DOCUMENTS

| | | | |
|---|---|---|---|
| 3,549,831 | 12/1970 | Forney | 2/8 X |
| 3,579,638 | 5/1971 | Davis et al. | 2/8 |
| 3,688,126 | 8/1972 | Klein | 340/148 X |
| 3,873,804 | 3/1975 | Gordon | 219/147 |
| 3,890,646 | 6/1975 | Fassett et al. | 2/8 |
| 4,039,803 | 8/1977 | Harsch | 219/147 |

Primary Examiner—B. A. Reynolds
Assistant Examiner—Keith E. George
Attorney, Agent, or Firm—Thomas H. Murray

[57] ABSTRACT

A protective welding lens assembly for use as the eyepiece of a welding helmet in which the lens assembly can be changed from a light-transmitting condition to an essentially opaque condition of very small light transmission, and vice versa, in response to an electrical signal and wherein the electrical signal for changing the light-transmitting characteristics of the lens assembly is controlled by energy emanating from the mouth of the user of the welding helmet. Preferably, the lens assembly comprises a liquid crystal light shutter; however any lens assembly can be used which can be electrically actuated to change its light-transmitting characteristics. A transducer is disposed within the welding helmet so as to be in front of the mouth of the welder when the helmet is positioned over his face. The transducer can comprise either a microphone responsive to sound from the welder's mouth or a pressure transducer responsive to blowing from the welder's mouth. An electrical signal generated by the transducer is then used to control the light-transmitting characteristics of the lens assembly.

6 Claims, 4 Drawing Figures

WELDING HELMET LENS ASSEMBLY

BACKGROUND OF THE INVENTION

In the past, various systems have been devised for automatically changing the light-transmitting characteristics of a welding helmet lens assembly in response to the existence of a welding arc. In such systems, the welder can readily see through the lens assembly under ambient light conditions when a welding arc does not exist; however, when a welding arc is struck, the lens assembly automatically becomes substantially opaque so that the eyes of the welder are protected from the intense light of the arc. An automatic lens assembly of this type eliminates the necessity for continually flipping the helmet from a raised position down to a protective position where the lens covers the eyes of the welder before an arc is struck between the electrode and the workpiece. One such automatic lens assembly is shown, for example, in Gordon U.S. Pat. No. Re. 29,684 where the lens assembly comprises a liquid crystal light shutter together with an electrical circuit which applies a suitable electrical potential to a liquid crystal film to change the same from a uniform light-transmitting condition to a uniform approximately opaque condition of very small light transmission when a welding arc exists.

In most automatic lens assemblies utilized in the prior art, the lens assembly is caused to change from a light-transmitting to an opaque condition in response to an electrical signal generated either by photocell means or a current surge through a power cable leading to the welding electrode. Sensing a surge of current in the power cable usually requires the use of a device closely adjacent the power cable which senses the surge in current, together with an electrical lead connecting the sensing device to circuitry in the welding helmet for controlling the liquid crystal light shutter. The electrical lead, however, is clumsy and can impede free movement of the welder.

A photocell which senses the welding arc, on the other hand, does not require any physical connection to the welding apparatus; however, welding helmets utilizing photo detectors are normally limited to use in buildings which are protected from sunlight. Otherwise, if the welding helmet is used outdoors, the light from the sun may trigger the photocell to cause the lens assembly to become essentially opaque when a welding arc does not, in fact, exist.

SUMMARY OF THE INVENTION

In accordance with the present invention, a protective automatic lens assembly is provided for welding helmets wherein the light-transmitting characteristics of the lens assembly are controlled by energy emanating from the mouth of the user of the helmet rather than by an optical pickup. In this respect, transducer means is positioned within the helmet so as to be in front of the mouth of the user when the helmet is in its lowered position where it protects the welder's eyes. The transducer means can comprise, for example, a microphone responsive to sound emanating from the mouth of the user or a pressure transducer responsive to blowing from the mouth of the user.

In the preferred embodiments of the invention, an electrical signal generated by the transducer is applied to a level detector, the output of which is utilized to trigger a flip-flop circuit. In one stable state of the flip-flop, the lens assembly will be in a light-transmitting condition and in its other stable state, the lens assembly will be substantially opaque. Thus, if the user makes a sound loud enough, or if he gently blows on the transducer, the lens assembly can be made to change from a light-transmitting opaque condition just before a welding arc is struck. Similarly, when the arc is extinguished, a sound from the welder of sufficient amplitude, or blowing from the welder's mouth, will trigger the flip-flop to cause the lens assembly to revert to its original condition where it is light-transmitting.

To assure that sound other than that emanating from the welder's mouth will not trigger the lens assembly, a directional sound detecting system can be employed wherein two microphones are disposed within the helmet in a plane extending perpendicular to the path of sound emanating from the welder's mouth. The outputs of the two microphones are summed and passed through a narrow passband filter which will pass frequencies only within a narrow range of sound frequencies emanating from the welder's mouth. By spacing the microphones apart in an amount equal to about one-half the wavelength of the frequency which the filter will pass, a directional sound detection system is provided wherein sound traveling parallel to the plane of the two microphones at the frequency to which the filter is tuned will be substantially attenuated while that at right angles to the plane of the microphones coming from the welder's mouth will not. This minimizes the possibility of extraneous sounds, other than those made by the welder, from triggering the lens assembly to change its light-transmitting characteristics.

The above and other objects and features of the invention will become apparent from the following detailed description taken in connection with the accompanying drawings which form a part of this specification and in which.

Figure 1:
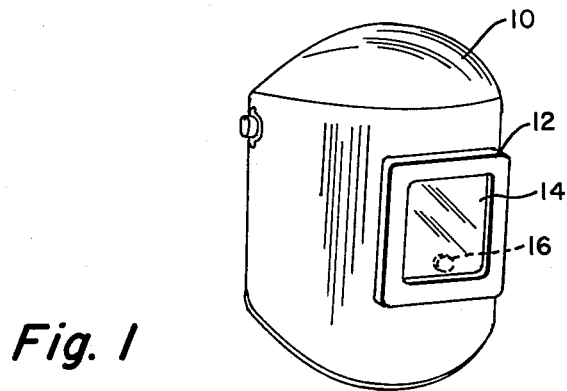
FIG. 1 is a perspective view of a welding helmet incorporating a liquid crystal light shutter assembly and with which the control system of the present invention may be used.

With reference now to the drawings, and particularly to FIG. 1, a welder's helmet 10 is shown provided with a lens assembly 12 provided with a liquid crystal light shutter 14. The liquid crystal light shutter 14, for example, may be of the type shown in Fergason U.S. Pat. No. 3,918,796 or Gordon U.S. Pat. No. Re. 29,684. For purposes of the present application, it will suffice to state that such a cell comprises a pair of parallel transparent plates having films of transparent conducting material on their facing surfaces. Between the transparent conducting films is a layer of nematic liquid crystal material. The transparent conducting films are rubbed at right angles to each other such that a twisted nematic structure results in the liquid crystal material which will rotate the plane of plane-polarized light by 90°. However, when an electrical field is applied across the liquid crystal material as by connecting the opposite terminals of a battery to the two transparent conducting films, the liquid crystal material will no longer rotate the plane of polarized light. Polarizers are disposed on either side of the cell. If the polarizers are parallel to each other, the liquid crystal light shutter will be essentially opaque in the absence of an applied electrical field (since the plane-polarized light is rotated through 90° in passing through the liquid crystal layer); however when an electrical field is applied to the twisted nematic structure, the liquid crystal material will no longer rotate the plane of polarized light. Under these conditions, the liquid crystal cell will no longer be substantially opaque and can be seen through under ambient light conditions. On the other hand, if the polarizers on opposite sides of the cell are crossed, then the cell will be light transmitting until an electrical field is applied across the liquid crystal material, whereupon the cell will appear substantially opaque. When the liquid crystal light shutter is substantially opaque in the presence of a welding arc, it has a light transmission of about 0.1%. Under these circumstances, the cell cannot be seen through under ambient light conditions; however the intense light of a welding arc can be seen. When the liquid crystal cell is light transmitting with the welding arc extinguished, it has a transmission of at least 6% whereby objects can be viewed through the cell under ambient light conditions.

While the present invention is particularly adapted for use with the liquid crystal light shutter of the type described above, it should be understood that it is also applicable to any light shutter which can be caused to change from light transmitting to an essentially opaque condition and vice versa in response to an electrical signal. In the past, it has been common to control the light-transmitting characteristics of the liquid crystal lens assembly 14 by means of photocells, one such photocell control arrangement being shown in Harsch U.S. Pat. No. 4,039,803. While a phototransistor is a convenient means of detecting the existence of a welding arc, such an arc is only a small portion of the field-of-view of the phototransistor comprising the area viewed by the welding helmet user. In this respect, visible light energy from the welding arc, at a distance of a few feet, is generally one and not more than ten times the magnitude of the ambient illumination in a welding shop. As a result, detecting the visible light from the welding arc is not an altogether satisfactory means of triggering the light shutter to a substantially opaque condition. While infrared wave energy can be detected and used to trigger the shutter, this also presents problems since the weld bead emits infrared energy after the arc is extinguished and can prevent the shutter from becoming light-transmitting. In either case, a photocell, whether it detects infrared or visible light energy, is not satisfactory for use outdoors where the sunlight is much brighter than the ambient light within a typical welding shop.

In accordance with the present invention, the light shutter 14 of FIG. 1 is triggered to change from a light-transmitting to a substantially opaque condition or vice versa by means of a transducer 16 positioned so as to be in front of the mouth of the user of the welding helmet and responsive to energy emanating from the mouth of the user. Transducer 16, for example, may be a microphone, or a pair of microphones as hereinafter described, which are responsive to voice signals emitted by the welder. On the other hand, transducer 16 may simply comprise a pressure transducer which will act to switch the liquid crystal light shutter from a light-transmitting to opaque condition or vice versa by simply blowing on the transducer.

Figure 2:
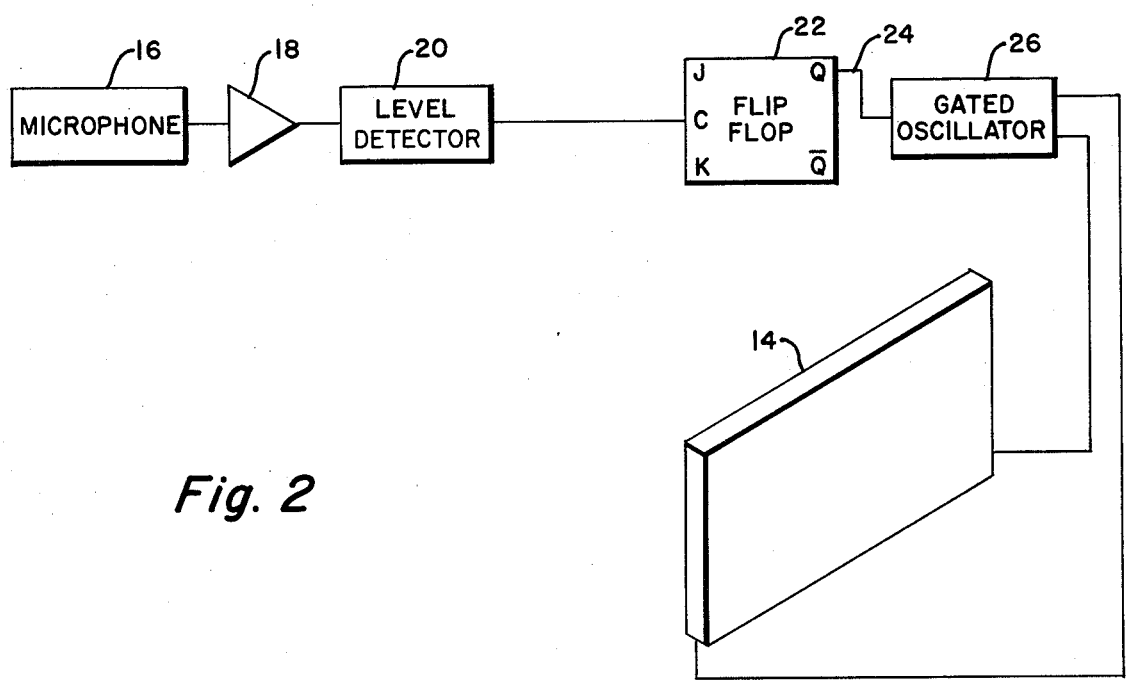
FIG. 2 is a schematic circuit diagram of one embodiment of the invention wherein a liquid crystal light shutter is controlled in response to sound emanating from the mouth of the user of a welding helmet.

One type of control system utilizing a microphone is shown in FIG. 2. The microphone 16 is connected through an amplifier 18 to a level detector 20 which will produce an output only when the amplitude of the signal generated by the microphone 16 exceeds a predetermined limit. Assuming that the signal from the microphone 16 does exceed the limit determined by the level detector 20, a signal at the output of the level detector will trigger flip-flop circuit 22 to change its stable states, thereby producing an output on lead 24 which triggers a gated oscillator 26 to apply an electrical field across the liquid crystal layer of the shutter 14. The shutter may be provided with crossed polarizers on its opposite sides such that it will transmit light until an audible sound of sufficient amplitude triggers the flip-flop 22 to change stable states. At this point, the field applied across the shutter 14 will untwist, causing the crossed polarizers to block light such that the shutter becomes substantially opaque. Upon receipt of a second audible signal by the microphone 16 of sufficient amplitude, the flip-flop 22 will flip back to its original stable state, thereby disabling the oscillator 26 and causing the liquid crystal cell 14 to revert to its light-transmitting state. Level detector 20 acts to insure that extraneous sounds of relatively low amplitude will not trigger the flip-flop 22. If desired, it is possible to insert into the circuit of FIG. 2 a filter which will pass only certain frequencies such that a particular word such as "stop" or "go" will have to be emitted by the welder before the flip-flop will be actuated. As will be understood, it is also possible to use parallel polarizers in the embodiment of FIG. 2, in which case actuation of the oscillator 26 will cause the light shutter to switch from an opaque to a light-transmitting condition. In either case (i.e., crossed or parallel polarizers), the light shutter will remain in one of its two states until the next sound causes it to reverse.

Figure 3:
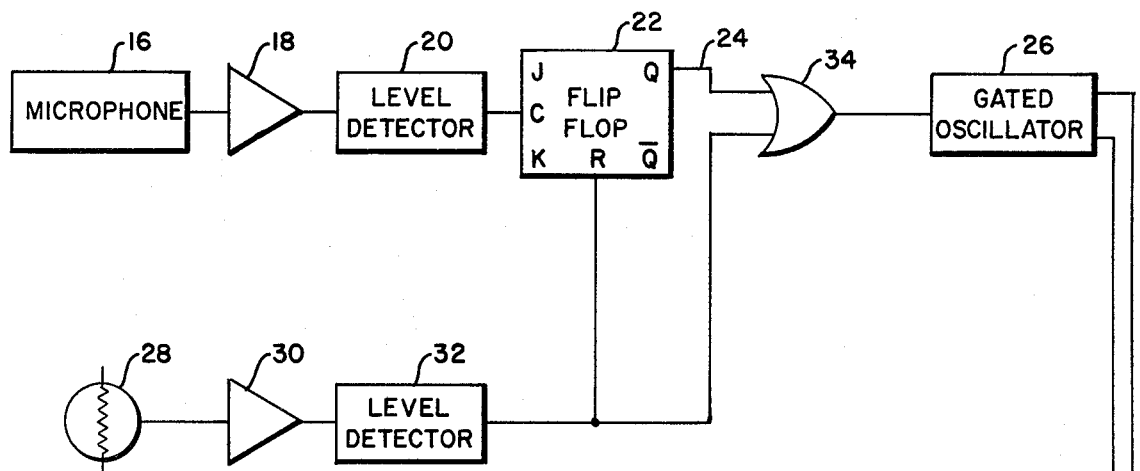
FIG. 3 is a schematic circuit diagram, similar to that of FIG. 2, but wherein control by voice signals is augmented by a photocell control system.
Figure 3:
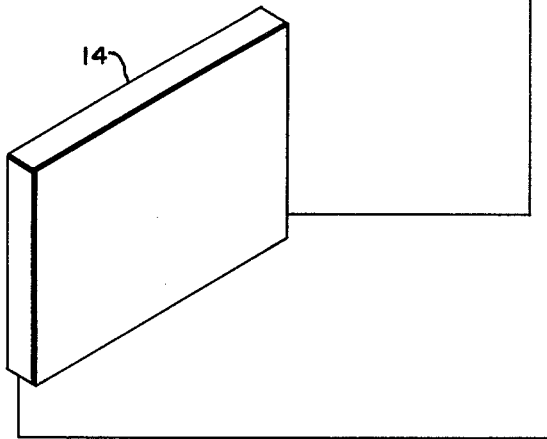

FIG. 3 illustrates an alternative embodiment of the invention wherein both a photocell and microphone are utilized in parallel to control the liquid crystal light shutter 14. Elements in FIG. 3 which correspond to those of FIG. 2 are identified by like reference numerals. In this case, however, a photocell 28 is exposed to the light from the welding arc and is connected through amplifier 30 and level detector 32 to an OR gate 34. Applied to the other input of the OR gate 34 is the output of the flip-flop on lead 24. A signal from the level detector 32 also acts to reset the flip-flop 22. In the arrangement of FIG. 3, cross polarizers are used on the liquid crystal light shutter 14 rather than parallel polarizers such that the shutter 14 will transmit light until an electrical field is applied across its liquid crystal layer. Regardless of whether an audible sound is made into the microphone 16 to cause the light shutter 14 to switch from a light-transmitting to an opaque condition upon existence of a welding arc, the photocell 28 will detect the welding arc and cause the shutter 14 to become opaque, thereby protecting the welder's eyes even though the welder should forget to emit an audible sound prior to striking the arc. By providing an inverter at the output of OR circuit 34 it is, of course, possible to use parallel rather than cross polarizers such that a signal from photocell 28 will act to turn off the oscillator 26 to cause the cell to become opaque.

Figure 4:
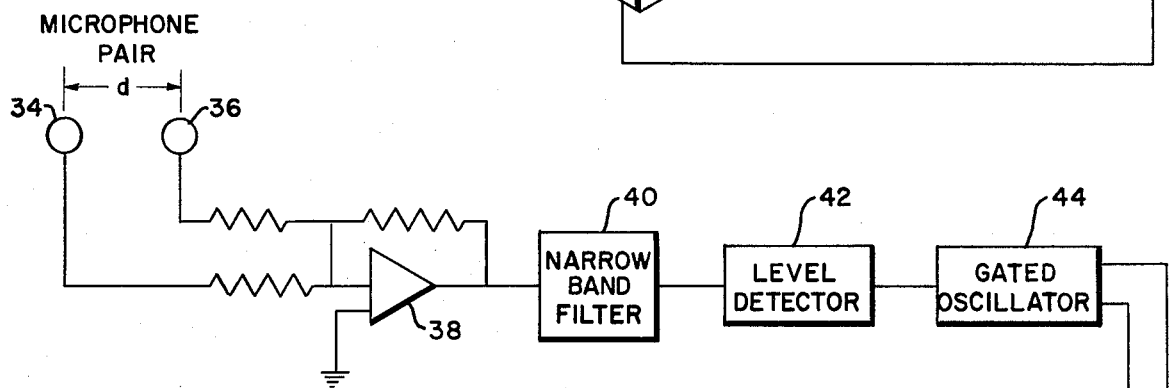
FIG. 4 is a schematic circuit diagram of the invention wherein a pair of spaced microphones is used to control a liquid crystal light shutter so as to achieve direction sensitivity.
Figure 4:
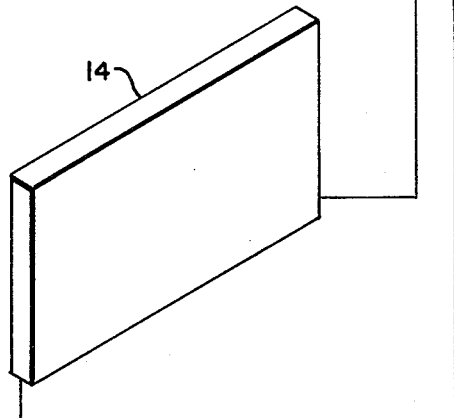

In FIG. 4 the embodiment of the invention is shown wherein two microphones 34 and 36 are employed rather than a single microphone. The microphones 34 and 36 lie in a common plane in front of the mouth of the user of the welding helmet, which plane will extend at substantially right angles to energy emanating from the mouth of the welder. The outputs of the two microphones 34 and 36 are summed in summing amplifier 38 and applied to a narrow bandpass filter 40 to a level detector 42 which, in turn, controls a gated oscillator 44 to trigger the liquid crystal light shutter 14 in the manner described above. The two microphones 34 and 36 are spaced apart by an amount equal to one-half the wavelength of the signal passing through narrow bandpass filter 40. That is, the distance d between the two microphones 34 and 36 is determined by the formula:

$$d = 1100 \text{ ft/sec}/2f$$

where f is the center frequency of the narrow bandpass filter 48 and 1100 ft/sec is the speed of sound in air. Under these circumstances, where the distance d between the microphones 34 and 36 is determined from the foregoing equation, soundwaves received in a plane extending parallel to the plane in which the microphones 34 and 36 are positioned will be out of phase with respect to each other and thus will cancel. Similarly, signals impinging on the microphone from any direction other than at right angles to the plane in which the microphones lie, will be at least partially attenuated. Only the wave energy emanating from the mouth of the user which is at right angles to the plane in which the microphones are located will not be attenuated. Accordingly, signals emanating from the right or left of the welder's face will have very little effect on the system; whereas signals emanating from the mouth of the welder will produce a large amplitude signal at the output of amplifier 38 since they are in phase and will pass through the narrow bandpass filter 40 and will trigger level detector 42 and gated oscillator 44.

Although the invention has been shown in connection with certain specific embodiments, it will be readily apparent to those skilled in the art that various changes in form and arrangement of parts may be made to suit requirements without departing from the spirit and scope of the invention.

I claim as my invention:

1. In a welding helmet, the combination of a lens assembly the light-transmitting characteristics of which can be changed in response to an electrical signal, electrical circuitry for controlling the light-transmitting characteristics of said lens assembly, a pair of spaced microphones in said electrical circuitry carried within said helmet and positioned so as to be in front of the mouth of the user of the helmet when the helmet is covering the face of the user, means for summing the outputs of the microphones, and means in the electrical circuitry for controlling the light-transmitting characteristics of the lens assembly in response to the summed outputs.

2. The combination of claim 1 wherein said lens assembly comprises a liquid crystal light shutter.

3. The combination of claim 2 including a gated oscillator actuable in response to energy directed toward said microphones for applying an electrical field across said liquid crystal light shutter.

4. The combination of claim 1 including a narrow passband filter connected to the output of said summing means, the signal passing through said filter acting to control said light-transmitting characteristics.

5. The combination of claim 4 wherein said microphones are spaced in a plane disposed in front of the mouth of the user of the welding helmet, said plane extending substantially perpendicular to the path of energy emanating from the mouth of the user.

6. The combination of claim 5 wherein the microphones are spaced apart in an amount equal to:

$$1100 \text{ ft/sec}/2f$$

where f is the center frequency of the narrow passband filter.

* * * * *